US006322583B1

(12) United States Patent
Tu et al.

(10) Patent No.: US 6,322,583 B1
(45) Date of Patent: *Nov. 27, 2001

(54) MEDICAL DEVICE AND METHODS THEREOF

(76) Inventors: Hosheng Tu; Lily Chen Tu, both of 2151 Palermo, Tustin, CA (US) 92782

( * ) Notice: Subject to any disclaimer, the term of this patent is extended or adjusted under 35 U.S.C. 154(b) by 0 days.

This patent is subject to a terminal disclaimer.

(21) Appl. No.: 09/046,224

(22) Filed: Mar. 23, 1998

(51) Int. Cl.$^7$ ..................................................... A61F 7/00
(52) U.S. Cl. ........................... 607/96; 606/169; 433/216; 15/22.1
(58) Field of Search ................... 607/96, 98, 99, 607/100, 101; 15/22.1, 167.1; 601/139, 141, 142; 433/86, 98, 99, 103, 114, 118, 119, 122, 216; 606/149, 159

(56) References Cited

U.S. PATENT DOCUMENTS

| 5,176,677 | * | 1/1993 | Wuchinich | 606/46 |
| 5,327,501 | * | 7/1994 | Kato et al. | 382/269 |
| 5,456,662 | | 10/1995 | Edwards et al. | 604/22 |
| 5,651,157 | | 7/1997 | Hahn | 15/22.1 |
| 5,735,280 | | 4/1998 | Sherman et al. | 607/96 |
| 5,948,009 | * | 9/1999 | Tu | 607/96 |
| 5,977,087 | * | 11/1999 | Pehrson et al. | 514/53 |

OTHER PUBLICATIONS

Gabriel Spera "The Next Wave in Minimally Invasive Surgery" Medical Device & Diagnostic Industry p. 36–44 (Aug. 1998).

* cited by examiner

Primary Examiner—John P. Leubecker
Assistant Examiner—R. Kearney (57) ABSTRACT

A medical device for treating gingivae or reducing the mass of cellular tissue, wherein an elongated tubular element comprises at least one electrode disposed of at its distal section, the energy generating means, and means for generating vibration at the distal section of the tubular element to effect the heat treatment and the vibrational massage therapy for the targeted tissue.

3 Claims, 7 Drawing Sheets

MEDICAL DEVICE AND METHODS THEREOF

The present invention generally relates to an improved device and methods for medical and dental purposes, and more particularly, to such a device and methods for providing appropriate heat treatment in a patient by delivering thermal energy to the gingivae site, or other tissue, with vibrational massage therapy.

BACKGROUND OF THE INVENTION

The gingivae are the gums and consist of a dense, fibrous connective tissue that attaches to the underlying bone and to the necks of the teeth. Gingivae are covered with a smooth mucous membrane, which is continuous with the mucous membrane of the lips and cheek, and is reflected into the tooth sockets where it is continuous with the periosteum. More teeth are lost by people over 35 because of periodontal disease (socalled pyorrhea) than from any other cause. Over half of our population beyond age 35 has developed some form of this disease. Many of these people are unaware of this condition because it is usually painless and progresses very slowly.

The simplest and most common form of the diseases is an inflammation of the gums known as gingivitis. It begins with a slight swelling along the gum margin of one or more teeth. The gum tissue in the area may have a slightly different color. As the condition grows worse, the puffiness and color change become more pronounced. The "collar" of the gum tissue loses its tight adaptation to the tooth surface, and the tissue bleeds on slight pressure.

If the disturbance is not treated, the gum tissue may gradually separate from the tooth and a pocket may form between the soft gum tissue and the hard tooth surface. The gingivitis, which is more superficial, has now developed into a more deep-seated condition called periodontitis. Bacteria, saliva and food debris collect in the pockets and intensify the destructive process. The bone adjacent to this area disappears, more attaching tissue is lost, and the pocket deepens and widens. Eventually, the tooth loosens, and in the process of chewing, additional irritation can occur.

The dentist may have to surgically remove the gum tissue that has been separated from the tooth during pocket formation. This procedure eliminates areas of stagnation and irritation, and it produces a greater surface area on the tooth, which needs to be kept clean.

Surgery exposes a patient to greater risks, due to infection and other health reasons. A less invasive approach using RF therapeutic protocols, has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, when coupled with a temperature control mechanism, can supply precise energy to the device-to-tissue contact site to obtain the desired thermal energy for treatment.

To be more efficient in RF energy ablation, the electrode with a vibration capability is used to simultaneously deliver the massage therapy to the target tissue. Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula, and RF energy is applied to the uvula tissue to cause internal lesions. However, Edwards et al. does not disclose a catheter to ablate tissue, in which there is the capability for simultaneously delivering radiofrequency energy and vibrational massage therapy.

Therefore, there is a need for an improved medical device and methods using radiofrequency energy to treat gingivae or tumors, while applying vibrational massage therapy.

SUMMARY OF THE INVENTION

In general, it is an object of the present invention to provide a method and an improved medical device for generating heat, to treat gingivae, polyps, prostate, tumors, or cellular tissues. It is another object of the present invention to provide a device in which vibrational massage therapy can be applied to the gingivae, polyps, prostate, tumors, or the targeted cellular tissues, for intimate contact. It is another object of the present invention to provide a method and a device for monitoring the temperature of the medical device, and to control the temperature by utilizing a temperature control mechanism and/or algorithm. The location of the temperature sensor means is preferably at the proximity of the tip of the medical device. It is still another object of this invention to provide a method and a device for treating gingivae, polyps, prostate, tumors, or cellular tissues in a patient by delivering a therapeutic agent to the targeted site.

Briefly, heat is generated by applying a suitable energy source to a device, which is comprised of an electrode means, in contact with the body tissue. A suitable energy source may consist of radiofrequency energy, microwave energy, ultrasonic energy, alternating current energy, or laser energy. The energy can be applied to the canker sore, the gingivae, the polyps, tumors, prostate, or other cellular tissues through the electrode means. A DIP (dispersive indifferent pad) type electrode, that contacts the patient, is connected to the Indifferent Electrode Connector on the RF generator. When using an alternating current electrical outlet, the generator should be grounded to avoid electrical interference. Heat is controlled by the power of the RF energy being delivered and by the delivery duration. The standard RF energy generator means, and its applications through the electrode means to a patient, are well known for those who are skilled in the art.

In a further embodiment, means for generating vibration at the distal section comprises a motor mounted in the cavity of the handle, which has a rotatable motor shaft, an elongated connecting shaft having a first end, to which the electrode means is connected, and a second end connected to the handle, a weight eccentrically mounted on the motor shaft with respect to the motor shaft axis, so as to rotate eccentrically, so that when the motor shaft rotates, the electrode vibrates. In another embodiment, means for generating vibration at the distal section comprises an ultrasonic generating means.

In one embodiment, the device is leak-proof so that the therapeutic agent, in either fluid phase or gel phase, can be forced under a positive pressure to flow inside the lumen of the medical device from its proximal end to the distal end. The fluid is vented through the at least one opening at the proximity of the electrode means to effect the therapeutic purpose to the targeted tissue site.

The method and device of the present invention has several significant advantages over other known systems or techniques to treat the canker sore, the gingivae, the polyps, prostate, tumors, or other cellular tissues. In particular, the device system comprising of the electrode means, using RF energy as a heat source, in this invention, and simultaneously delivering vibrational massage therapy to the targeted tissue sites, results in a more efficient therapeutic effect, which is highly desirable in its intended application on canker sores, the gingivae, the polyps, tumors, prostate, other cellular tissues, or other medical applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
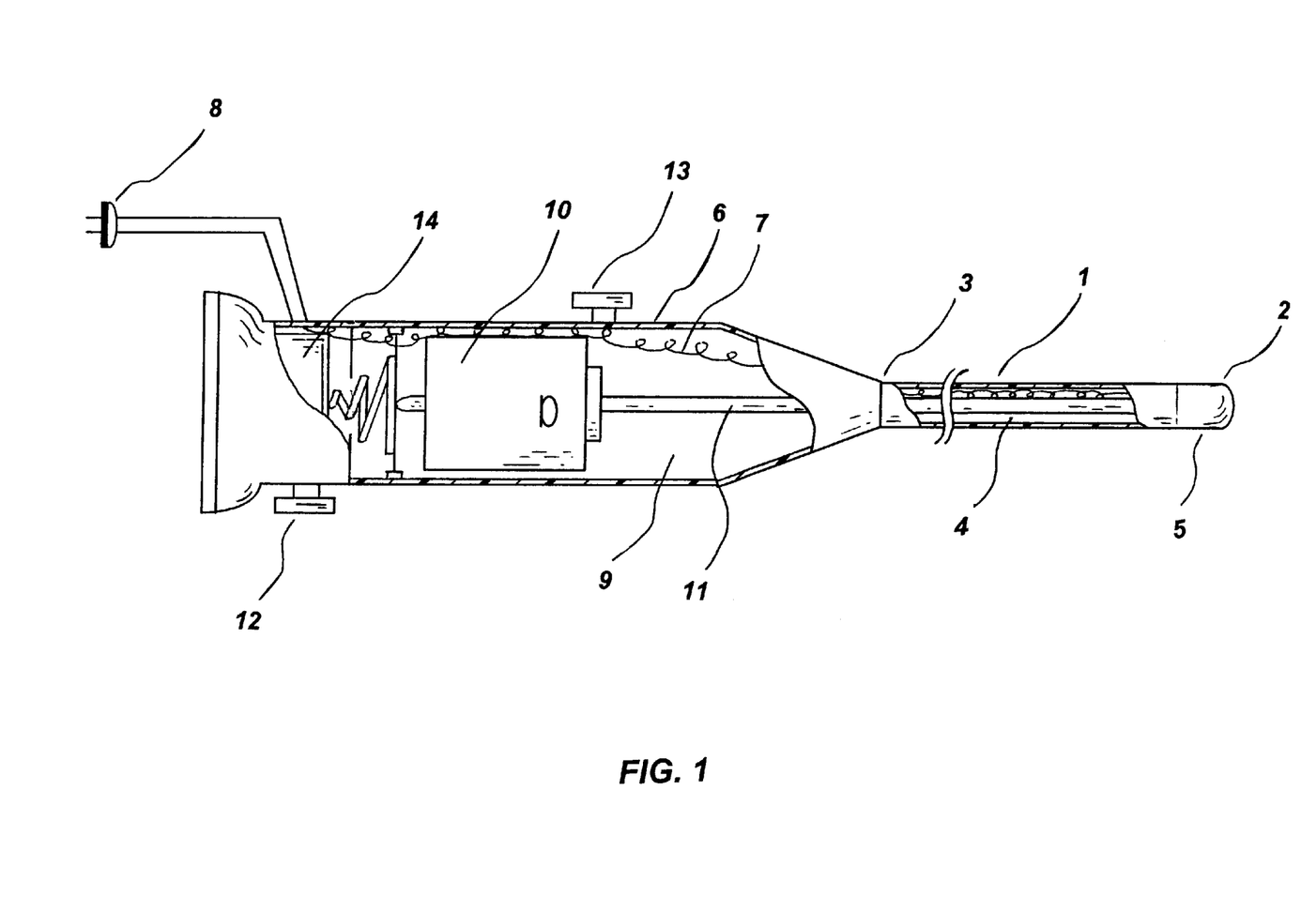
FIG. 1 is an over-all view of the medical device, having an electrode means with heat generating source, and a vibration generating means, constructed in accordance with the principles of the present invention.

Referring to FIGS. 1 to 5, what is shown is an embodiment of the medical device system, simultaneously applying radiofrequency energy and applying a vibrational therapeutic massage to treat the gingivae, tumors, prostate, polyps, or cellular tissues of a patient. As shown in FIG. 1, the ablation device in the form of an elongated tubular element 1 comprises a distal section, a distal end 2, a proximal end 3, and at least one lumen 4 extending therebetween; wherein at least an electrode means 5 is disposed of at the distal section, and wherein the electrode means 5 has a conductive surface for contacting the target tissue. The "target tissue" in this patent indicates the gingivae, tumor, prostate, polyp or other cellular tissues. The medical device also comprises a handle 6 secured at the proximal end 3 of the tubular element 1, wherein the handle has a cavity 9; and means for supplying energy from an external energy means to the electrode means 5 of the medical device system. The energy source can be selected from the group of radiofrequency energy, microwave energy, ultrasonic energy, alternating current electrical energy, or laser energy. A conducting wire 7, which is connected by a connector 8 at the proximal end of the handle 6, is used to transmit the RF energy or other type of energy. The very distal section of the medical device is somewhat flexible and bendable. The energy supply is controlled by an on-off switch button 13 located conveniently on the handle 6.

There is a cavity 9 inside the handle 6, in which a motor 10 is located. A shaft 11 is located within the lumen 4 of the tubular element 1 and is connected to the motor 10 and to an appropriate point in the proximity of the distal end 2 of the tubular element 1. In one embodiment, a battery means 14, which is located at the proximal end of the cavity 9 of the handle 6, is used to supply the energy to the motor 10. In an alternate embodiment, the motor 10 is powered by an alternating current (AC) through a power-input plug (not shown). In either case, the power supply is controlled by an on-off switch button 12 located conveniently at the proximal end of the handle 6.

Optionally, the distal portion of the device comprises a coil-like element so that the very distal portion close to the distal end is manually bendable or steerable. The outer surface of the medical device, except the electrode means at its distal end, is not conductive.

Figure 2:
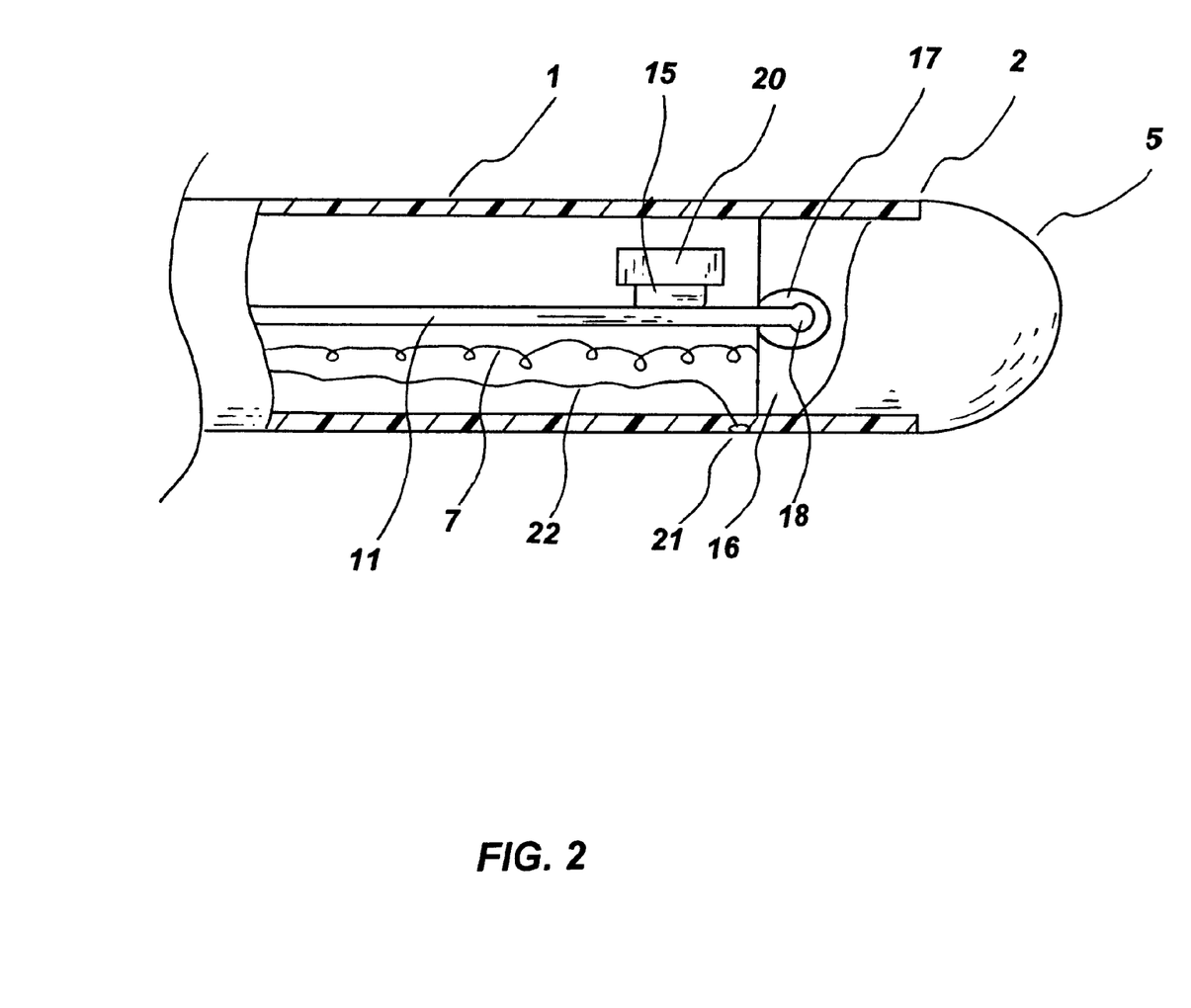
FIG. 2 is a cross-sectional view of the distal portion of the medical device in FIG. 1.

FIG. 2 is a cross-sectional view of the distal portion of the medical device. The elongated tubular element 1 comprises an electrode means 5 at the distal end 2 of the tubular element 1, wherein the electrode means 5 has a stem 16, which is used to fit the electrode means 5 into the distal end 2 of the tubular element 1. A receptor hole 17 on the stem 16 of the electrode means 5 is employed for loosely holding the distal end 18 of the shaft 11 inside the receptor hole 17. The shape of the distal end 18 is in the form of a ball-type end, so that the end 18 stays securely inside the hole 17, even at the vibration step. One energy conducting wire 7 is located within the lumen 4 of the tubular element 1. One end of the conducting wire 7 is secured and connected to the electrode means 5 at the distal end 2 while the other end of the conducting wire 7 is secured to a contact pin of the connector 8, wherefrom the conducting wire 7 is connected to an external RF generator means (not shown) or other energy source.

Attached to the distal portion of the shaft 11, there is an eccentric weight 20. The eccentric weight 20 is either secured to the shaft 11 directly, or through a connecting means 15. The eccentric rotation of the weight 20 places the tip electrode 5 into vibration via the shaft 11 due to the unbalancing effect of the eccentric weight 20. The vibrational amplitude of the tip electrode 5 of the tubular element 1 is determined by the geometry of the shaft 11, the mass and configuration of the weight 20, and the rotational speed of the motor 10, among other factors.

In one embodiment, a temperature sensing means 21 is disposed close to the electrode means 5. An insulated temperature sensor wire means 22 passes from the temperature sensing means 21 at the distal end, to an external temperature control mechanism through the outlet connector 8. The energy delivery is controlled by the measured temperature from the temperature sensing means 21, a closed-loop temperature control mechanism and/or algorithm. When the measured temperature rises to the preset high-limit point, the temperature control mechanism sends out a signal to cut off the energy supply. In a similar manner, when the measured temperature drops to the preset low-limit point, the temperature control mechanism sends out a signal to activate the energy supply. The control mechanism can be a proportional mode, a derivative mode, an integral mode, or a combination of the above modes.

Figure 3:
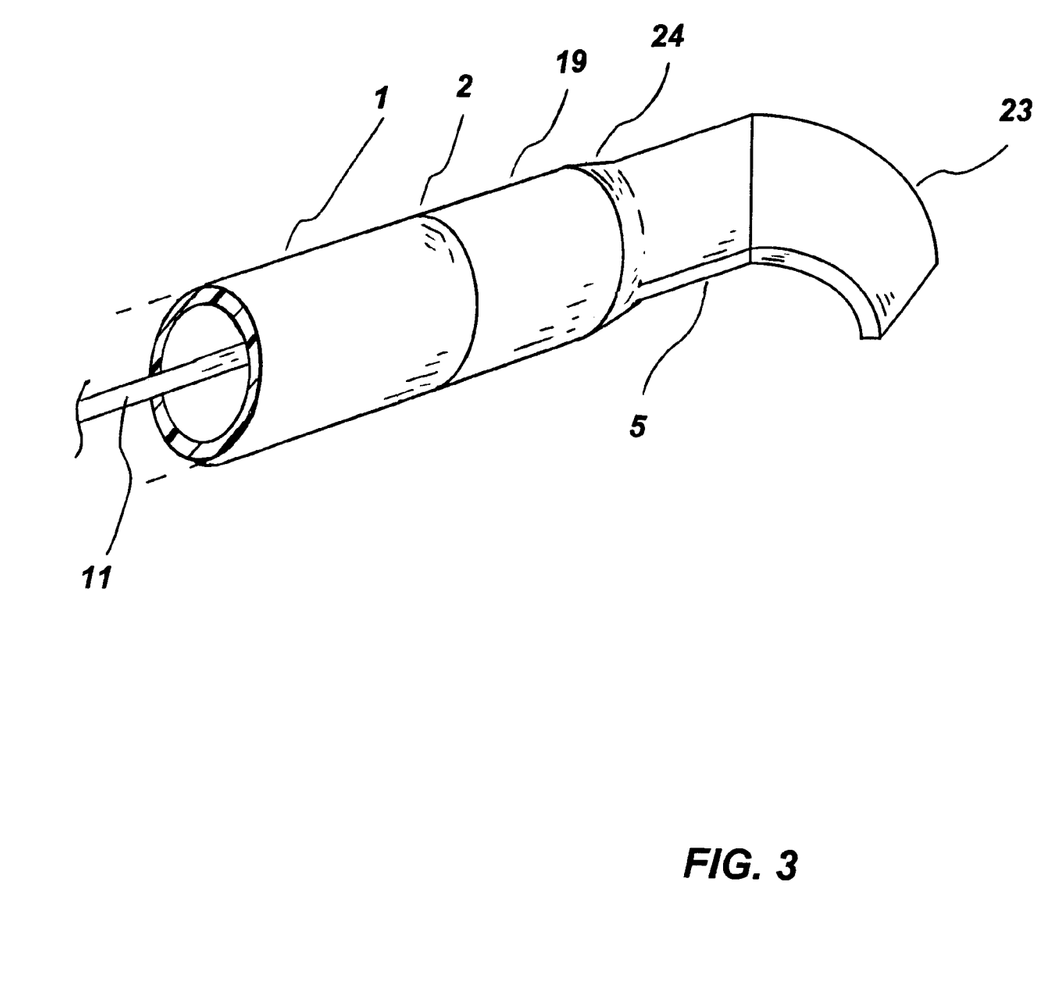
FIG. 3 shows a perspective view of the medical device for treating gingivae disease.

FIG. 3 shows a perspective view of the medical device for treating gingivae disease. The electrode means 5 at the distal end 2 of the tubular element 1 comprises a cylindrical body 19, a tapered section 24, and a curved U-shaped end element 23. The U-shaped element 23 is designed to have proper configuration to fit into the gum portion of a patient from over the edge of the gum lines. The length of the edge of the end element 23 can be from 1 mm to 5 mm. The U-shaped element 23 of the electrode means 5 is to intimately contact the gum to its maximum contacting extent. Intimate contact is to effect the heat treatment on the gingivae with association of the vibrational massage therapy.

Figure 4:
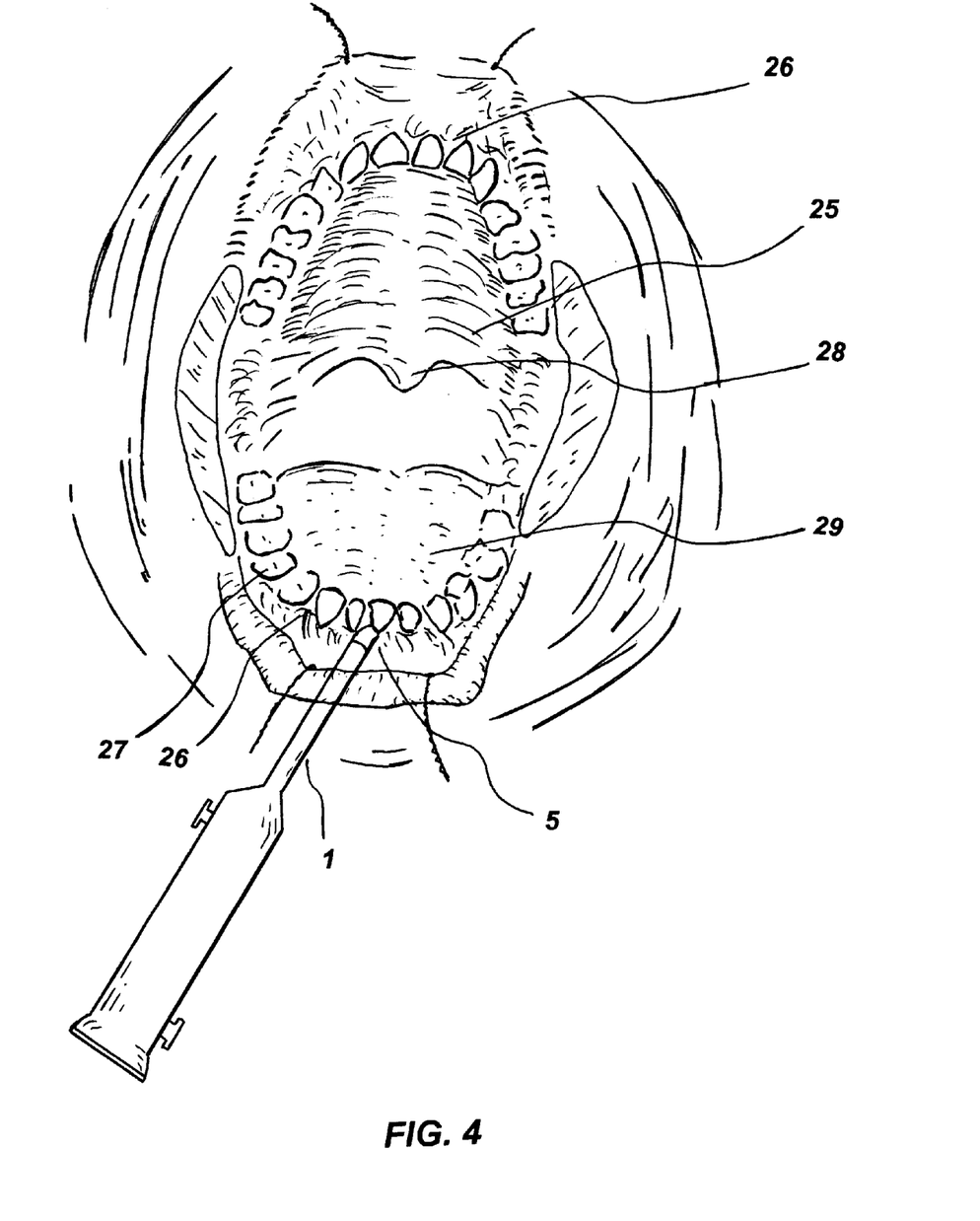
FIG. 4 shows a front view of the gingivae being treated by the medical device of the present invention.

FIG. 4 shows a front view of the gingivae being treated by the medical device of the present invention. For illustration purpose, the mouth 25 of a patient is briefly shown here. The gingivae 26 are the gums, and consist of a dense, fibrous connective tissue. The gingivae are attached to the underlying bone and to the necks of the teeth 27. The uvula 28 and the tongue 29 are located within the cavity of the mouth. The distal section of the tubular element 1 has the capability of vibration. The electrode means 5 contacts the tissue gingivae 26 during its vibration state to effect the vibrational massage therapy. In one embodiment, the external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the target gingivae site, through the electrode means 5 of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode means and applying the vibrational massage therapy topically, the gum disease can be treated.

Figure 5A:
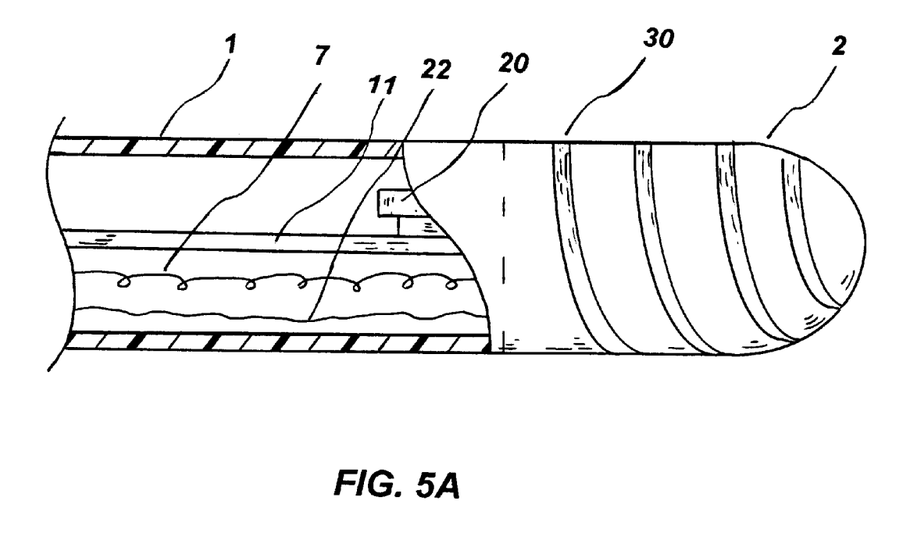
FIG. 5A to 5C shows alternate configurations of the electrode means of the present invention.
Figure 5B:
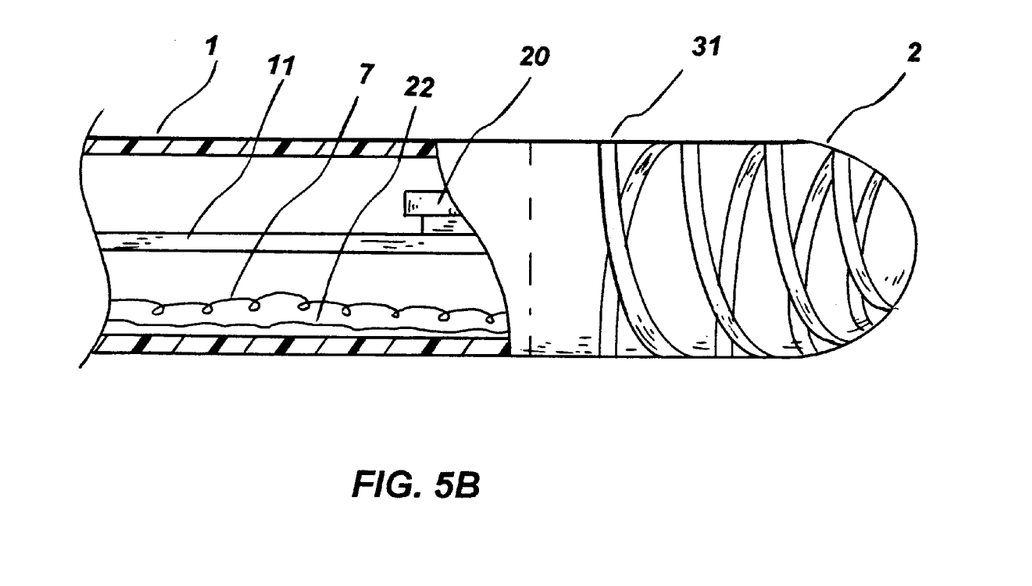
Figure 5C:
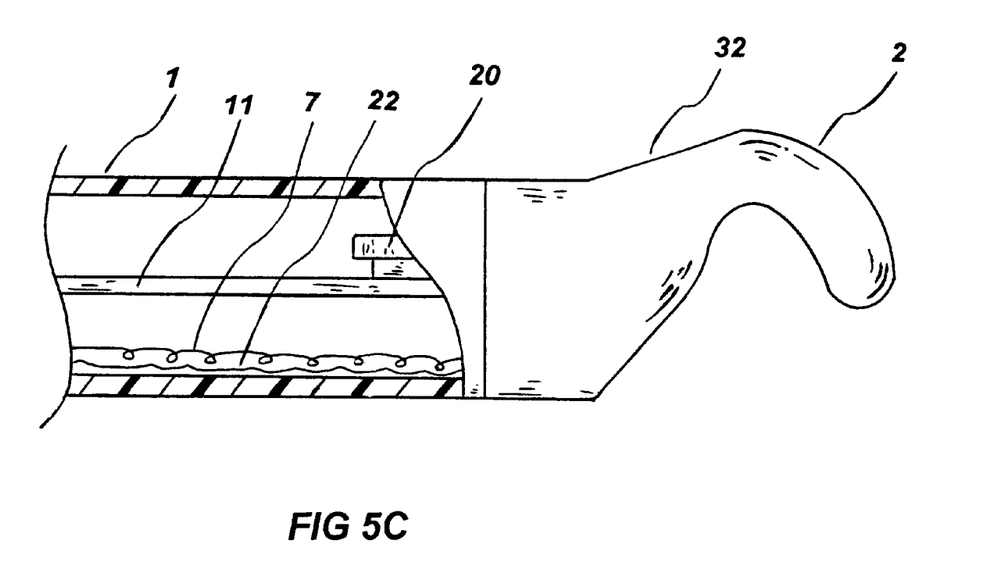

FIG. 5A to 5C shows several alternate configurations of the electrodes means of the present invention. In FIG. 5A, the alternate electrode means 30 at the distal end 2 of the tubular element 1 comprises a coil-type electrode, which is secured on the exterior surface of the distal end 2 of the tubular element 1. A conducting wire 7 is connected to the coil-type electrode 30 for delivery of the energy to this electrode. In FIG. 5B, another alternate electrode means 31 comprises a mesh-type electrode, which is secured on the exterior surface of the distal end 2 of the tubular element 1. Again, a conducting wire 7 is connected to the mesh-type electrode 31 for delivery of the energy to this electrode. In FIG. 5C, a third alternate electrode means 32 comprises a ball-type electrode having a special anchoring configuration at one side of the electrode means. A conducting wire 7 is connected to the ball-type electrode 32 for delivery of the energy to this electrode. Other convenient types of electrodes are also suitable for use in this invention.

The method for treating the gingivae disease of a patient comprises: (a) inserting a medical device into the mouth of a patient, wherein the device has a distal section, a distal end, a proximal end, a lumen extending therebetween, a handle, which has a cavity, attached to the proximal end of the device, wherein an electrode means is disposed of at the distal end, and wherein the means for generating vibration at the distal section is located within the handle; (b) contacting the electrode means of the device against the gingivae of a patient; (c) applying energy means to the electrode means of the device to effect heat treatment of the gingivae; and (d) starting the vibration step to the distal section of the device to effect the vibrational massage therapy to the gingivae. The means for generating vibration at the distal section comprises a motor mounted in the cavity of the handle, which has a rotatable motor shaft, an elongated connecting shaft having a first end to which the electrode means is connected, and a second end connected to the handle, a weight eccentrically mounted onto the motor shaft, with respect to the motor shaft axis, so as to rotate eccentrically, so that when the motor shaft rotates, the electrode vibrates.

Alternatively, the method of treating the polyps of a patient comprises: (a) directing a medical device to the polyps site of a patient, wherein the device has a distal section, a distal end, a proximal end, a lumen extending therebetween, a handle, which has a cavity, attached to the proximal end of the device, wherein an electrode means is disposed of at the distal end, and wherein the means for generating vibration at the distal section is located within the handle; wherein the means for generating vibration at the distal section comprises a motor mounted in the cavity of the handle, which has a rotatable motor shaft, an elongated connecting shaft having a first end to which the electrode means is connected, and a second end connected to the handle, a weight eccentrically mounted onto the motor shaft with respect to the motor shaft axis so as to rotate eccentrically, so that when the motor shaft rotates, the electrode vibrates; (b) contacting the electrode means of the device against the polyps site of a patient; (c) applying RF energy means to the tip electrode of the device to effect heat treatment of the polyps; and (d) starting the vibration to the distal section of the device to effect the vibrational massage therapy to the polyps site.

In a particular embodiment, the material for the electrode means of this invention consists of conductive metals such as platinum, iridium, gold, silver, stainless steel, Nitinol (a nickel and titanium alloy), or an alloy of these metals. The electrode means is selected from the group of a coil electrode, a tubular electrode, a cap electrode, a U-shape electrode, a mesh electrode, or a ball electrode with a special anchoring configuration.

From the foregoing description, it should now be appreciated that a catheter system for gingivae, polyps, prostate, tumors, or cellular tissues treatment, comprising a suitable energy source and a vibrational massage therapy, with an optional fluid irrigation capability has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of treating polyps of a patient, the method comprising:
    (a) directing a medical device to the polyps site of the patient, wherein the device has a distal section, a distal end, a proximal end, a lumen extending therebetween, a handle attached to the proximal end of the device, electrode means for providing energy to a tissue disposed at the distal end, energy means for providing energy through a conducting wire to said electrode means, means for generating rotational vibration at the distal section located within the handle, wherein the means for generating rotational vibration at the distal section comprises a motor mounted in a cavity of the handle, which has a rotatable motor shaft, an elongated connecting shaft having a first end to which the electrode means is connected, and a second end connected to the handle, a weight eccentrically mounted onto the motor shaft, with respect to the motor shaft axis, so as to rotate eccentrically, so that when the motor shaft rotates, the electrode means vibrates;
    (b) contacting the electrode means of the device against the polyps site of a patient;
    (c) applying RF energy through said energy means to the electrode means of the medical device to effect heat treatment of the polyps; and
    (d) starting rotational vibration to the distal section of the device to effect a vibrational massage therapy to the polyps site.

2. The method for treating polyps of a patient of claim 1, wherein the electrode means is selected from the group consisting of a coil electrode, a tubular electrode, a cap electrode, a U-shape electrode, a mesh electrode, and a ball-type electrode having a special anchoring configuration.

3. The method for treating polyps of a patient of claim 1, wherein a frequency of rotational vibration is within the range of 60 to 1000 cycles per minute.

* * * * *